United States Patent [19]

Di Schiena

[11] Patent Number: 4,866,067
[45] Date of Patent: Sep. 12, 1989

[54] 6-PIPERIDINO-2,4-DIAMINOPYRIMIDINE-3-OXIDE SALT OF 3-CARBOXYPYRIDINE N-OXIDE AND TOPICAL, RELATED COMPOSITIONS

[75] Inventor: Michele G. Di Schiena, Milan, Italy

[73] Assignee: Ricerche De Schiena s.n.c del Dr. Michele Giuseppe Di Schiena & C., Milan, Italy

[21] Appl. No.: 129,743

[22] Filed: Dec. 7, 1987

[51] Int. Cl.$^4$ .......................................... A61K 31/505
[52] U.S. Cl. ..................................... 514/275; 544/298
[58] Field of Search ......................... 544/298; 514/275

[56] References Cited

U.S. PATENT DOCUMENTS 3,464,987  9/1969  Ursprung et al. ................... 544/298
3,637,697  1/1972  Anthony et al. ..................... 544/298

OTHER PUBLICATIONS

*The New England Journal of Medicine* (Dec. 18, 1980), vol. 303, No. 25, pp. 1480–1481, "Reversal of Baldness in Patient Receiving Minoxidil for Hypertension", Anthony R. Zappacosta, MD.

*Primary Examiner*—Mary C. Lee
*Assistant Examiner*—Zinna Northington
*Attorney, Agent, or Firm*—Oblon, Spivak, McClelland, Maier & Neustadt

[57] ABSTRACT

The 6-piperidino-2,4-diaminopyrimidine-3-oxide salt of 3-carboxypyridine N-oxide, according to formula (I)

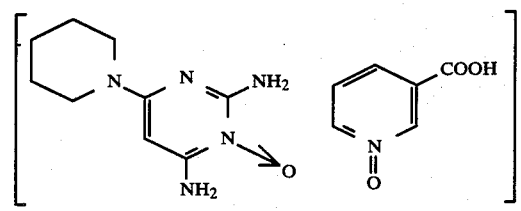

is described.

The compound (I) is useful in cosmetic and pharmaceutical field for the treatment of hair loss or of pathologic forms, such as alopecia, exfoliative dermatitis, etc. Topical formulations containing the compound (I) are also described.

4 Claims, No Drawings

6-PIPERIDINO-2,4-DIAMINOPYRIMIDINE-3-OXIDE SALT OF 3-CARBOXYPYRIDINE N-OXIDE AND TOPICAL, RELATED COMPOSITIONS

DESCRIPTION

Object of the present invention is the 6-piperidine-2,4-diaminio-pyrimidine-3-oxide salt of 3-carboxypyridine N-oxide according to formula (I)

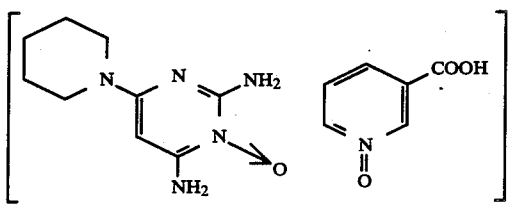

The compound (I) is active in promoting the growth of hairs and of other body piles and can therefore be employed in cosmetic, pharmaceutical and veterinary field in the form of appropriate topical formulations.

Said 2,4-diaminopyrimidine derivate, which is the basic component of the salt of formula (I), is known also under the common international name of Minoxidil: it is already employed as anti-hypertensive drug in human therapy and its use by topical application in the treatment of the common baldness and spotted alopecia has been described.

As a consequence of Minoxidil being insoluble in water, the resulting liquid formulations are glycol or polyalcohol-based and their topical applications are therefore unpleasant, tending to grease the scalp.

On the contrary, the salt object of the invention, being soluble in water, can therefore be easily formulated as water-based composition.

The acid component of salt (I), 3-carboxypyridine N-oxide, known also as oxyniacic acid, is already employed in systemic therapy as lipemia-controlling drug, particularly the cholesterol and tryglyceride fraction, and as vaso-activating agent, free from particular side-effects.

These very properties of oxyniacic acid allow to reasonably assume that the higher activity of the novel compound of formula (I), compared to Minioxidil alone. is to be ascribed, as far as hair growth is concerned, to a synergistic mechanism whereby the lipidic component of the scalp, the altered composition of which is regarded as responsible for some forms of baldness, is favourably controlled and an effective micro-circulation, considered also very important for the optimum preservation of hair health, is restored.

The novel compound object of the invention is, moreover, remarkably soluble in water and, for this peculiar property, particularly suitable for the utilization in formulations based only, or prevailingly, on water, which are particularly appropriate in the trichological field.

Both the systemic toxicity and the cutaneous endurableness fall within the ranges already known for topically administered Minoxidil.

Compound (I) can therefore the advantageously formulated as lotion, cream, spry, shampoo, gel, brilliantine, bandoline, preferably based only, or prevailingly, on water. The formulations object of the invention can include, besides the compound of formula (I), other complementary active ingredients in addition to the usual carriers and excipients, such as perfumes, stabilizers, drystuffs, etc.

The invention obviously concerns those formulations too, wherein oxyniacic acid and Minoxidil do not meet stechiometric ratios; in this case the non salified portion of either component has activity complementary to the compound of formula (I).

The formulations of the invention include the active ingredient in concentration ranging from 0,1% to 10% and are to be generally applied on the interested area once or more per day.

The preparation of the novel compound is carried out according to techniques well-known in the art; f.i. it can be prepared in water by reacting nearly stechiometric amounts of Minoxidil and 3-carboxypyridine N-oxide.

The compound of the invention can be easily prepared by employing other suitable solvents, such as anhydrous or partly dehydrated methanol, ethanol, isopropanol, etc.

The compound of formula (I) is isolated according to usual techniques, such as, for example, the solvent evaporation, the precipitation by non-solvents, etc.

The following exemples are only aimed at illustrating the invention and not at limiting it.

EXAMPLE 1

To a suspension of 2,0 g of Minoxidil in 50 ml of water 1,39 g of 3-carboxypyridine N-oxide areadded. The resulting solution can be employed as such to form compositions for topical application. Alternatively, the compound can be isolated as a solid, for example by evaporating the water, preferably under reduced pressure.

According to this procedure, the compound of formula (I) is obtained preferably pure, in theoretical yield.
I.R. Spectrum (KBr)

Characteristic bands:

| | |
|---|---|
| 3320, 3100 cm$^{-1}$ | attributable to —NH$_2$ group |
| 2940, 2850 cm$^{-1}$ | attributable to CH$_2$ group (piperidine) |
| 1650 to 1600 cm$^{-1}$ | attributable to COO$^-$, NH$_2$ and C=C groups |
| 1240 cm$^{-1}$ | attributable to N—O group |

EXAMPLE 2

2,09 g of Minoxidil and 1.39 g of 3-carboxypyridine N-oxide are dissolved in 100 ml of 95% ethanol. The resulting solution can be employed as such or suitably diluted and/or added with adjuvants or complementary materials.

Alternatively, the solid compound can be isolated by thoroughly evaporating the solvent or by adding ethyl ether as precipitating agent to a partially evaporated solution.

The solid compound, no matter how it was obtained, chemically conforms with that of Example 1.

EXAMPLE 3

Formulations

In the following are reported compositions of formulations of the compound according to formula (I).

| (a) Lotion: | |
|---|---|
| Compound of formula (I) | 3.40 g |
| Ascorbic nicotinamide complex | 3 g |

|     |                                         |       |
| --- | --------------------------------------- | ----- |
|     | Preserved water up to                   | 100 g |
| (b) | Lotion:                                 |       |
|     | Compound of formula (I)                 | 3.40 g |
|     | Biotin                                  | 0.3 g |
|     | Vitamin B3                              | 0.3 g |
|     | Vitamin B1                              | 0.1 g |
|     | Vitamin B2                              | 0.1 g |
|     | Brewer's yeast (water-soluble fraction) | 1.0 g |
|     | Inositol hexanicotinate                 | 0.1 g |
|     | 95° Ethanol                             | 50.0 g |
|     | Deionized and preserved water up to     | 100 g |
| (c) | Lotion:                                 |       |
|     | Compound of formula (I)                 | 3.4 g |
|     | Betanaphthol                            | 0.3 g |
|     | Salicylic acid                          | 0.1 g |
|     | Resorcinol                              | 0.5 g |
|     | Capsicum tincture                       | 0.5 g |
|     | 70° Alcohol up to                       | 100 g |
| (d) | Lotion: (5 ml monodose bottles with containing cap) | |
|     | Content of the cap:                     |       |
|     | Compound of formula (I)                 | 0.170 g |
|     | Content of the bottle:                  |       |
|     | 95° Ethanol                             | 1.0 ml |
|     | Perfumed water up to                    | 5.0 ml |
|     | Use: In use, press the cap and break the protective membrane for dissolving the solid into the liquid; the resulting solution is applied evenly on the interested area. | |
| (e) | Foam:                                   |       |
|     | Compound of formula (I)                 | 5.0 g |
|     | Propylene glycol                        | 9.0 g |
|     | Isopropyl alcohol                       | 4.5 g |
|     | Cetyl alcohol                           | 1.8 g |
|     | Stearic acid                            | 0.9 g |
|     | Laureth-4                               | 4.7 g |
|     | Perfumed water up to                    | 100.0 g |
|     | Propellant 114                          | 10.0 g |
| (f) | Cream:                                  |       |
|     | Compound of formula (I)                 | 3.0 g |

|     |                            |       |
| --- | -------------------------- | ----- |
|     | Minoxidil                  | 0.5 g |
|     | Isopropyl miristate        | 12.0 g |
|     | Diglycol stearate          | 10.0 g |
|     | Triethanolamine stearate   | 5.0 g |
|     | Lanolin                    | 5.0 g |
|     | Cholesterin                | 4.0 g |
|     | Lecithin                   | 1.0 g |
|     | Antioxidant BHT            | 0.1 g |
|     | Preserved water up to      | 100.0 g |
| (g) | Gel:                       |       |
|     | Compound of formula (I)    | 3.4 g |
|     | Sodium Carboxymethylcellulose | 9.0 g |
|     | Preserved water up to      | 100.0 g |

I claim:

1. 6-Piperidino-2,4-diaminopyrimidine-3-oxide salt of 3-carboxypyridine N-oxide having the formula (I)

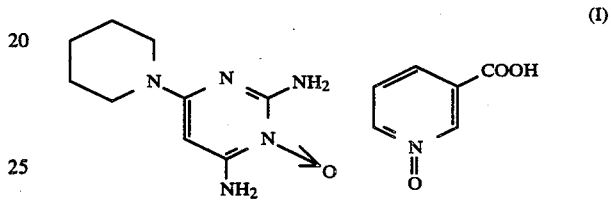

2. A pharmaceutical composition comprising a hair growth promoting effective amount of the compound of formula (I) according to claim 1 and a pharmaceutically acceptable carrier.

3. The pharmaceutical composition of claim 2, wherein said pharmaceutical carrier is water or alcohol.

4. The pharmaceutical composition of claim 2, wherein said composition is in the form of a lotion, cream, spray, shampoo, gel, brilliantine, or vandoline.

* * * * *

UNITED STATES PATENT AND TRADEMARK OFFICE
CERTIFICATE OF CORRECTION

PATENT NO. : 4,866,067
DATED : Sep. 12, 1989
INVENTOR(S) : Michele G. Di Schiena It is certified that error appears in the above-identified patent and that said Letters Patent is hereby corrected as shown below:

On the title page, item [73]:

The Assignee is incorrectly indicated, "Ricerche De Schiena s.n.c. del Dr. Michele Giuseppe De Schiena & C." should be:

--Ricerche Di Schiena s.n.c. Del Dr. Michele Giuseppe Di Schiena & C.--

Signed and Sealed this

Sixteenth Day of October, 1990

Attest:

HARRY F. MANBECK, JR.

*Attesting Officer*  *Commissioner of Patents and Trademarks*